United States Patent
Hastings et al.

[19]

[11] Patent Number: 5,865,720
[45] Date of Patent: Feb. 2, 1999

[54] EXPANDABLE AND RETRIEVABLE RADIATION DELIVERY SYSTEM

[75] Inventors: Roger N. Hastings, Maple Grove; Michael J. Urick, Rogers, both of Minn.

[73] Assignee: SciMed Life Systems, Inc., Maple Grove, Minn.

[21] Appl. No.: 812,022

[22] Filed: Mar. 6, 1997

[51] Int. Cl.$^6$ ..................................................... A61N 5/00
[52] U.S. Cl. ................................................................ 600/3
[58] Field of Search .................... 600/1–8; 606/191–194, 606/198

[56] References Cited

U.S. PATENT DOCUMENTS

| | | | |
|---|---|---|---|
| 5,059,166 | 10/1991 | Fischell et al. | 600/3 |
| 5,176,617 | 1/1993 | Fischell et al. | 600/3 |
| 5,199,939 | 4/1993 | Dake et al. | 600/3 |
| 5,213,561 | 5/1993 | Weinstein et al. | 600/7 |
| 5,302,168 | 4/1994 | Hess | 600/3 |
| 5,308,356 | 5/1994 | Blackshear, Jr. et al. | 606/194 |
| 5,354,257 | 10/1994 | Roubin et al. | 600/7 |
| 5,411,466 | 5/1995 | Hess | 600/3 |
| 5,484,384 | 1/1996 | Fearnot | 600/3 |
| 5,498,227 | 3/1996 | Mawad | 600/3 |
| 5,503,613 | 4/1996 | Weinberger | 600/3 |
| 5,540,659 | 7/1996 | Teirstein | 604/104 |
| 5,545,132 | 8/1996 | Fagan et al. | 604/96 |
| 5,556,389 | 9/1996 | Liprie | 604/264 |
| 5,605,530 | 2/1997 | Fischell et al. | 600/3 |
| 5,616,114 | 4/1997 | Thornton et al. | 600/3 |
| 5,618,266 | 4/1997 | Liprie | 604/21 |
| 5,674,177 | 10/1997 | Hehrlein et al. | 600/3 |

FOREIGN PATENT DOCUMENTS

| | | |
|---|---|---|
| 0 433 011 B1 | 6/1991 | European Pat. Off. . |
| 0 497 495 A2 | 8/1992 | European Pat. Off. . |
| 0 593 136 A1 | 4/1994 | European Pat. Off. . |
| 0 633 041 A1 | 1/1995 | European Pat. Off. . |
| 0 688 580 A1 | 12/1995 | European Pat. Off. . |
| 91 023 12 U | 6/1992 | Germany . |
| WO 93/04735 | 3/1993 | WIPO . |
| WO 94/25106 | 11/1994 | WIPO . |
| WO 94/26205 | 11/1994 | WIPO . |
| WO 95/07732 | 3/1995 | WIPO . |
| WO 95/19807 | 7/1995 | WIPO . |
| WO 95/26681 | 10/1995 | WIPO . |
| WO 96/06654 | 3/1996 | WIPO . |
| WO 96/10436 | 4/1996 | WIPO . |
| WO 96/13303 | 5/1996 | WIPO . |
| WO 96/14898 | 5/1996 | WIPO . |
| WO 96/17654 | 6/1996 | WIPO . |
| WO 96/22121 | 7/1996 | WIPO . |
| WO 97/18012 | 5/1997 | WIPO . |

OTHER PUBLICATIONS

*Radiotherapy of Intraocular and Orbital Tumors*, Springer–Verlak publisher, Berlin Heidelberg and New York, copright 1993, pp. 23–30 and 363–367.

Tjho–Heslinga et al., "Results of ruthenium irradiation of uveal melanoma", *Radiotherapy Oncology*, vol. 29, pp. 33–38, 1993.

Lommatzsch et al., "Radiation effects on the optic nerve observed after brachytherapy of choroidal melanomas with 106Ru/106Rh plaques", *Graefe's Arch. Clin. Exp. Ophthalmology*, vol. 232, pp. 482–487, 1994.

*Primary Examiner*—John P. Lacyk
*Attorney, Agent, or Firm*—Crompton, Seager & Tufte, LLC

[57] ABSTRACT

A device and method for irradiating human body vessel interior walls. One device includes a beta radiation emitting segmented metal tube disposed at the distal end of an elongate shaft. Another device includes a radioactive elastic sleeve mounted on a shaft. The device can be used to inhibit restenosis following angioplasty in coronary arteries. In use, the device can be advanced distally over the balloon portion of a positioned and deflated angioplasty balloon catheter, whereupon the balloon is inflated, pressing the radiation device into close contact with vessel walls. After a desired exposure period, the balloon is deflated, and the device, biased to contract, contracts with the balloon, allowing for ease of withdrawal from the patient.

20 Claims, 3 Drawing Sheets

OTHER PUBLICATIONS

Raloff, "Nuclear Medicine Gets Friendlier—Experimental Therapies Seek to Poison Just the Disease", *Science News*, vol. 152, Jul. 19, 1997, pp. 40–41.

Fackelmann, "Harbinger of a Heart Attack—Does a Protein in the Blood Foretell Heart Trouble", *Science News*, vol. 151, Jun. 14, 1997, pp. 374–375.

"Aids and Cancer Cured by Hyper–Oxygenation", *Now What*, Issue No. 1, 1987, Waves Forest, Monterey, California.

Li et al., "Reactive Oxygen Species Induce Apoptosis of Vascular Smooth Muscle Cell", *FEBS Letters*, 404, 1997, pp. 249–252.

Kalli, "Oxygen Emulsion The Question of Free Radicals", Internet Address http://www.livelinks.com/sumeria/oxy/rad2.html, Aug. 1, 1997.

Parry, "Reactive Oxygen Species in Living Systems—Sources: Biochemistry, and Role in Human Disease", Internet Address http://www.livelinks.com/sumeria/oxy/reactive-.html, Jul. 21, 1997 from *American Journal of Medicine*, vol. 91, No. 3C, Sep. 30, 1991, p.14S(9).

Block, "Peroxygen Compounds, Chapter 9", *Disinfection, Sterilization, and Preservation,* Fourth Edition, Lea & Febiger, Philadelphia, Copyright 1991.

Moore, "Free Radial Generation by Thyroid Peroxidase and Its Effects on Cells in Vitro", PhD. Dissertation, Group in Endocrinology–University of California, Berkeley, California, Dec. 1990.

EXPANDABLE AND RETRIEVABLE RADIATION DELIVERY SYSTEM

FIELD OF THE INVENTION

The invention relates generally to a device for providing radiation to the interior of human body vessel walls. More specifically, the invention relates to a radiation emitting device for mounting over balloon catheters which can be used to inhibit restenosis in blood vessels.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve use of a guide wire and catheter, possibly in combination with other intravascular devices. A typical balloon catheter has an elongate shaft with a balloon attached to its distal end and a manifold attached to the proximal end. In use, the balloon catheter is advanced over the guide wire such that the balloon is positioned adjacent a restriction in a diseased vessel. The balloon is then inflated and the restriction in the vessel is opened.

Vascular restrictions that have been dilated do not always remain open. In approximately 30% of the cases, a restriction reappears over a period of months. The mechanism of restenosis is not understood. The mechanism is believed to be different from the mechanism that caused the original stenosis. It is believed that rapid proliferation of vascular smooth muscle cells surrounding the dilated region may be involved. Restenosis may be in part a healing response to the dilation, including the formation of scar tissue.

Intravascular treatments, including delivery of radioactive radiation have been proposed as a means to prevent or reduce the effects of restenosis. For example, U.S. Pat. No. 5,199,939 to Dake et al. suggests that intravascular delivery of radiation may inhibit restenosis. Dake et al. suggest delivering radiation within the distal portion of a tubular catheter. Fischell, in the publication EPO 0 593 136 A1, suggests placing a thin wire having a radioactive tip near the site of vessel wall trauma for a limited time to prevent restenosis. Problems exist in attempting to provide uniform radiation exposure using a point or line source. Specifically, as the radiation varies inversely with the square of distance from a point source and inversely with distance from a line source laying off center near one vessel wall may significantly overexpose the nearby wall while underexposing the further away wall.

Bradshaw, in PCT publication WO 94/25106, proposes using an inflatable balloon to center the radiation source wire tip. In PCT publication WO 96/14898, Bradshaw et al. propose use of centering balloons which allow blood perfusion around the balloon during treatment. U.S. Pat. No. 5,540,659 to Tierstein suggests use of a helical centering balloon, attached to a catheter at points about the radiation source to allow perfusion through the balloon, between the balloon and radiation ribbon source.

Use of continuous centering balloons having a beta radiation source within significantly attenuates the beta radiation when the balloon is filled with inflation fluid and the balloon may also allow the radiation source to "warp" when placed across curved vessel regions, allowing the balloon to bend but having the central radiation source lying in a straight line between the two ends. Segmented centering balloons may improve the warping problem but may also increase beta attenuation by allowing blood to lie or flow between the beta source and vessel walls. Balloons allowing external perfusion in general have the aforementioned beta attenuation problem. What remains to be provided is an improved apparatus and method for delivering uniform radiation to vessel interiors to inhibit restenosis.

SUMMARY OF THE INVENTION

The present invention includes devices and methods for providing radiation to the interior of human body vessels. One device includes a radioactive tube disposed at the distal end of an elongate shaft. The tube should be long enough to treat the target site but can be segmented to provide increased flexibility for traversing tortuous vessel passages. One embodiment utilizes tubular segments bonded to the distal portion of the elongate shaft. Another device includes an elastic sleeve, impregnated with radioactive material, disposed on the distal portion of an elongate shaft. A preferred radiation source is a beta emitter, as beta radiation penetrates only a few millimeters into tissue, rather than through the tissue, patient, and into the operating room, as can be the case with gamma emitters.

In use, the device can be used immediately after angioplasty has been completed, while the angioplasty balloon catheter is still in position. The tubular, radioactive device can be advanced over the catheter shaft and over the deflated angioplasty balloon. With the tube in place over the balloon, the balloon is reinflated, expanding the tube into close contact with the vessel walls. The close contact brings the beta emitters into effective contact with the vessel walls. This eliminates the centering problem and resulting over and under exposure that can occur with non-centered line and point sources. A preferred method utilizes a perfusion angioplasty balloon which allows uninterrupted exposure of the radiation to the vessel without interrupting blood flow. After a desired exposure period, the balloon can be deflated. Upon deflation, the tubular device, being biased to contract, contracts with the contracting balloon. The device contracts sufficiently to be easily withdrawn from the patient.

In one method, the radiation device is distally preloaded onto a catheter balloon after angioplasty has been performed, the catheter and radiation device are then advanced together into position over the stenosis. In another method, the radiation device is distally preloaded onto an angioplasty balloon catheter prior to angioplasty. The angioplasty catheter, with radiation device in place over the balloon, is advanced into position, and angioplasty performed. The balloon may be inflated for a longer period than usual, to allow for irradiation of the vessel walls. In the distal preload methods, the radiation device is preferably disposed near the distal end of an elongate shaft.

The radiation source can be used within a sheath to prevent contact between the radiation source and blood. This allows reuse of the source, and possible reuse without sterilization of the source, as a sterile, disposable sheath can be used in place of a sterile radiation source. The present invention can be used both manually and in combination with automatically controlled afterloaders.

The present invention thus provides uniform radiation exposure at a small distance from vessel walls, allowing use of lower activity radiation sources. The generally tubular configuration removes the centering problem and the attendant under and over exposure problems. The segmented tubes allow flexibility through tortuous paths. The present invention is compatible with existing angioplasty catheters.

DETAILED DESCRIPTION OF THE PREFERRED EMBODIMENTS

Figure 1:
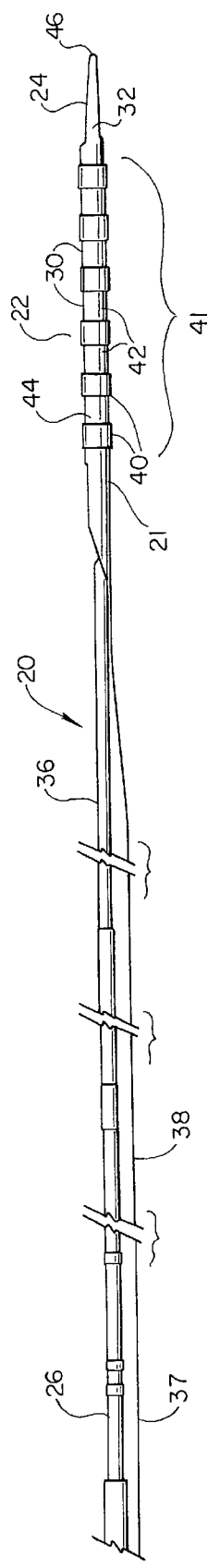
FIG. 1 is a fragmentary side view of a perfusion balloon catheter having a radiation device mounted thereover.

FIG. 1 illustrates a catheter 20 having a radiation device 21 mounted thereover. Catheter 20 is a perfusion balloon catheter including a shaft 36, a proximal portion 26, a distal portion 22, and a distal end 24. Catheter 20 includes a tapered nose 32 having a distal port 46. Catheter distal portion 22 includes an inflatable balloon 44 having an envelope 30. Catheter shaft 36 includes an inflation lumen (not shown in FIG. 1) in fluid communication with the interior of balloon 44.

Radiation device 21 includes an elongate shaft 38 having a proximal portion 37, a distal portion 39, and a plurality of segments 40 attached to the distal portion. Segments 40 are connected to each other with interconnecting segments 42. In the embodiment of FIG. 1, interconnecting segments 42 are a continuation of elongate shaft 38.

Figure 2:
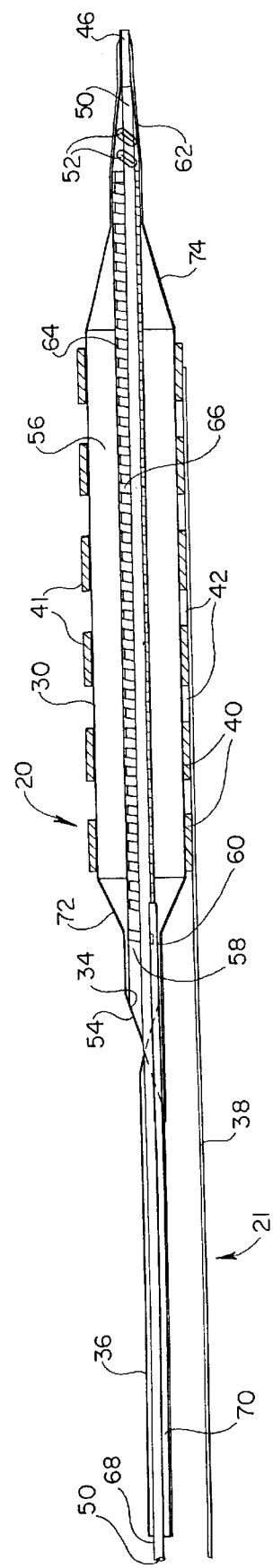
FIG. 2 is a fragmentary, enlarged view of a distal portion of the catheter and radiation device of FIG. 1.

Referring now to FIG. 2, catheter 20 and radiation device 21 are illustrated in more detail. A preferred catheter for use with radiation device 21 is a perfusion balloon catheter as illustrated by catheter 20. Catheter 20 includes a perfusion tube 64 having a series of reinforcing ribs 66 and a perfusion lumen 58 therethrough. Ribs 66 are provided to maintain lumen 58 in an open configuration against inward inflation pressure from balloon 44. Perfusing blood flows through proximal perfusion port 54, through a skived region 34, through perfusion lumen 58, and exiting through distal perfusion ports 52.

A preferred catheter includes a guide wire lumen, illustrated in FIG. 2 by a guide wire tube 68 defining a guide wire lumen 50 within. In the embodiment shown, guide wire tube 68 is contained within perfusion lumen 58 and extends distally through exit nose 32 out distal end or port 46. Balloon 44 includes an envelope 30 extending from a proximal waist 60, over a proximal shoulder 72, over the balloon major surface, over a distal shoulder 74, terminating in a distal waist 62. Balloon 44 includes a balloon interior space 56. Catheter shaft 36 contains an inflation lumen 70 in fluid communication with balloon interior 56.

Radiation device distal portion 39 has a generally tubular configuration 41, as indicated in FIG. 1, for ease in fitting over a balloon. In the embodiment of FIG. 2, the tubular configuration includes a series of segments 40 having a series of gaps 41 therebetween. Segments 40 divide the tubular configuration of device 21 into short segments, thereby allowing the device to maneuver through tortuous vessel passages not passable if the device was a continuous tube. Segments 40 are connected to each other with segment interconnectors 42. In the embodiment illustrated, segments 40 are secured to device elongate shaft 38. In a preferred embodiment, segments 40 are welded or soldered to a metal wire which forms device shaft 38. Preferred materials for device shaft 38 are a NiTi alloy or stainless steel. In one embodiment, a tubular configuration is formed from a single tube by cutting gaps into the tube wall such that the tube remains a single piece but having gaps sufficient to enable bending of the resulting segments around vessel turns and bends. In this embodiment, the segments are interconnected with the original tube material. Gaps 41 provide improved maneuverability but also can create discontinuities in radiation coverage in the gap regions. For this reason, gap size is minimized to allow sufficient flexibility while maintaining complete radiation coverage. Balloon 44 is illustrated in an inflated position, where segments 40 could be pressed into close proximity with vessel walls.

Segments 40 are biased so as to return to a less expanded position after having been expanded to a more expanded position, such as in contact with a vessel wall. While an ideal segment 40 is perfectly elastic and exhibits no permanent deformation after expansion, some inelastic deformation is allowable, providing the tubular segments return to an outside diameter small enough to be retracted from the patient.

Figure 3:
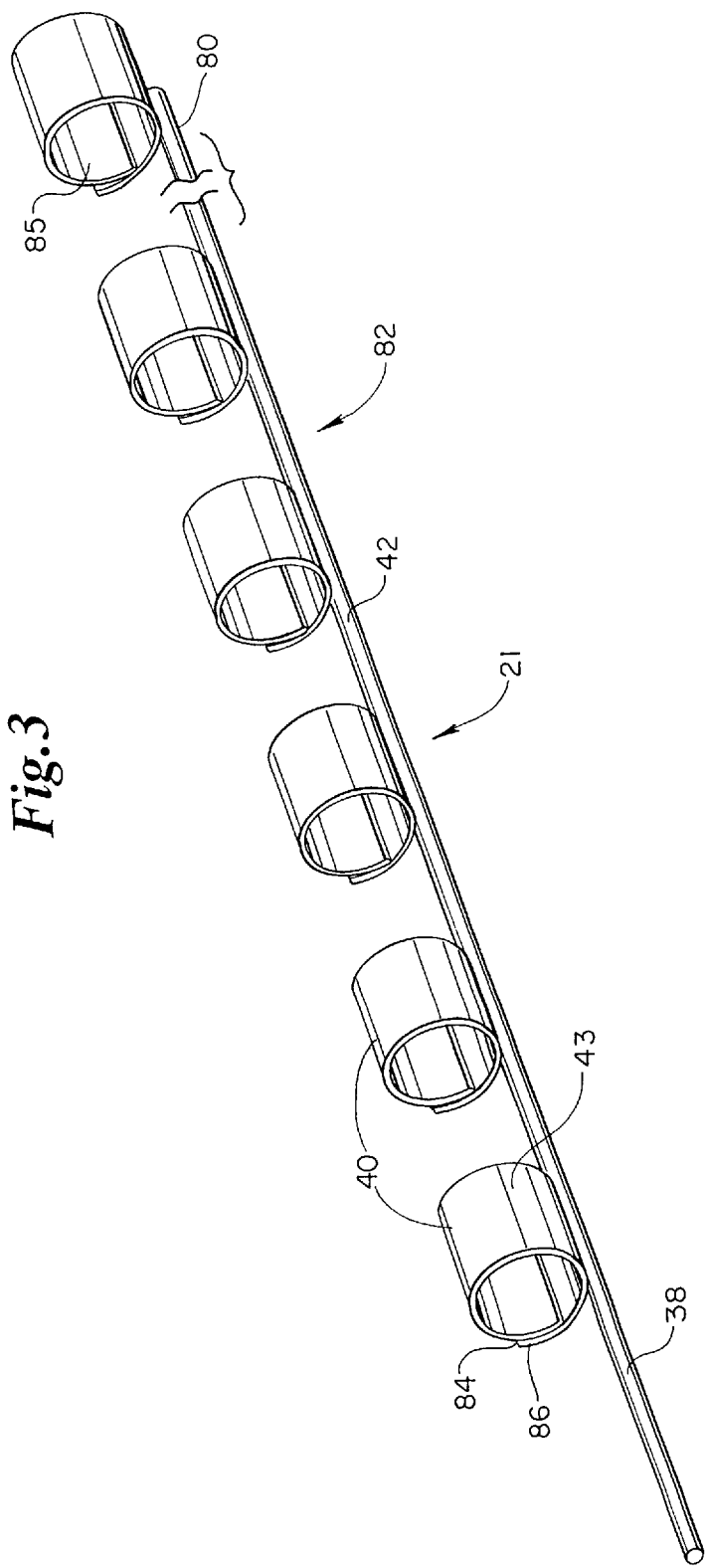
FIG. 3 is a fragmentary, enlarged, perspective view of the radiation device of FIG. 1.

Referring now to FIG. 3, radiation device 21 is shown in still more detail, extending to a distal end 80, with segments 40 defining a catheter passage or segment interior 85 therethrough. Tubular segments 40 have segment bodies 43 which have slits 84 therein. In the embodiment illustrated, slits 84 form an overlap 86 of segment body material. Slits 84 allow a catheter shaft 36, as shown in previous figures, to be maneuvered from exterior of device 21 to a position within the segment interiors 85 of the radiation device 21. This allows device 21 to be mounted over catheter shaft 36 while the catheter is inserted in the body. Overlap 86 allows for balloon expansion within segments 40 without losing significant radial radiation coverage due to the expansion of the segments.

Segments 40 are radioactive. In a preferred embodiment, segments 40 contain or are made from, at least in part, beta emitters. A preferred material for construction of segments 40 is Nickel-66 or a Nickel-66 coated with polytetrafluoroethylene. Nickel-66 emits low energy beta radiation and no gamma radiation. Nickel-66 has a half-life of 2.28 days, then converts to Copper-66 with a half life of 5.10 minutes during which time high energy beta radiation is emitted. The Copper-66 then decays into stable Zinc-66, which after 23 days allows disposal by ordinary means. Nickel-66 can be used in alloys such as Nickel—Titanium, NiTi.

Figure 4:
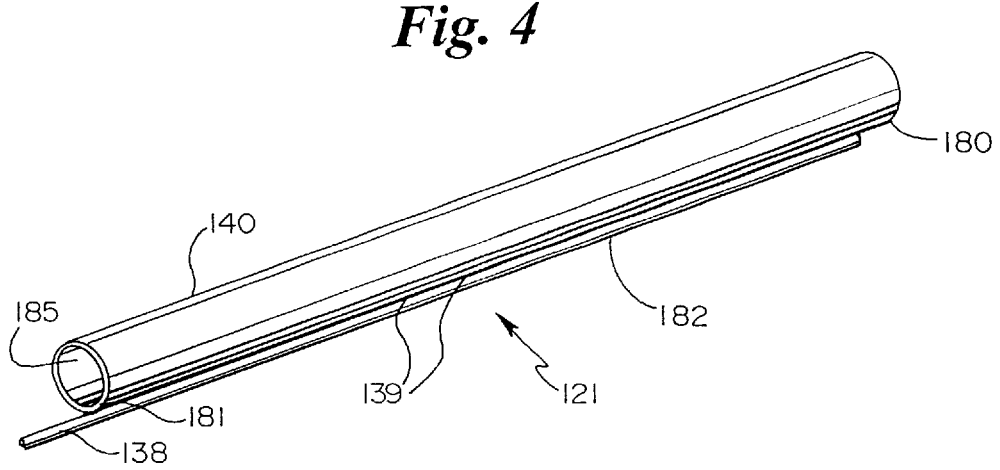
FIG. 4 is a fragmentary, perspective view of an elastic sleeve radiation device.

Referring to FIG. 4, another radiation device 121 is illustrated. Device 121 includes an elongate shaft 138 and a radioactive, elastic sleeve 140 disposed on a distal portion 182 of shaft 138. Sleeve 140 extends from a distal end 180 through a proximal end 181 and is preferably bonded to shaft 138 over distal portion 182 as indicated at 139. A sleeve lumen 185 extends through sleeve 140. Sleeve 140 in one embodiment is elastomeric. A preferred material for construction of the sleeve is polyurethane. A preferred radiation source is a beta emitter such as Nickel-66, admixed, compounded, or chemically part of the polymeric substance forming the sleeve. Sleeve 180 distal end is adapted to slide over a balloon proximal shoulder, expanding, when required, to slide over the balloon. The sleeve is sufficiently elastic to expand with an angioplasty balloon inflated within, yet contract with the deflating, contracting balloon to a size sufficiently small to retract from a patient.

In use, referring again to FIG. 2, radiation device 21 can be advanced over an already positioned balloon catheter or can be distally preloaded onto a catheter balloon outside a patient's body. In a preferred method, a guide wire is inserted into position within the patient, near or through the stenosis to be treated. A balloon angioplasty catheter is advanced into position over the guide wire, to the stenosed region. The balloon catheter is inflated under pressure, dilating the stenoses. The catheter is then deflated at least partially, reducing the balloon outside diameter. A radiation device such as device 21 is mounted over a proximal portion of the catheter shaft extending out from the patient. The radiation device is then advanced distally over the shaft, approaching the balloon proximal shoulder as illustrated by shoulder 72 in FIG. 2. A gradually sloping shoulder as illustrated in FIG. 2 is preferred for ease in advancing device 21 distally over the shoulder.

The device distal end is slid over the balloon proximal shoulder, which may expand the tubular segments of the device. With the tubular segments disposed over the balloon, the balloon can again be inflated, bringing segments 40 into close proximity or contact with the vessel wall. In a preferred method, the segments are pressed against the vessel walls sufficient to substantially preclude blood flow between segments 40 and the vessel walls. This presents multiple advantages. First, the radiation source, for example, segments 40, is brought within a close distance to the vessel walls, providing increased radiation exposure due to the inversely squared decrease in exposure with distance. Second, precluding blood flow between radiation source and vessel walls removes a source of attenuation of radiation, especially beta radiation which is significantly attenuated by fluids. Third, providing radiation at a small distance from the vessel wall allows for use of lower activity devices than would otherwise be possible, making for safer passage through the vasculature, where radiation exposure may not be desirable. Fourth, over the interior surface of the vessel, radiation exposure is relatively more uniform coming from a diffuse and close source compared to a more distant point or line radiation source. Vessel wall areas adjacent device intersegment gaps may not receive as much radiation as areas adjacent the segments. This relatively lower exposure can be alleviated by reducing the gap area and by repeating irradiation after moving the radiation device longitudinally. In embodiments not having perfect tubal radial symmetry, periodic tube rotation may alleviate effects of uneven exposure as well.

The radiation device is then held against the vessel walls for a desired exposure period. A preferred method utilizes a perfusion balloon catheter, allowing for a prolonged irradiation period, by allowing perfusing blood flow to downstream tissue. A non-perfusing catheter would require shorter irradiation periods, requiring higher radiation activity or periodic balloon deflation to allow for blood flow. It is recognized that very small vessels (<2.5 mm) may not require perfusion or long inflation time, depending on the source strength. After the desired exposure period, the balloon may be deflated, allowing the biased segments of the radiation device to contract to a smaller outside diameter. The segments should contract to a diameter sufficiently small such that withdrawal of the device from the patient does not present a problem.

In one method, the radiation device is withdrawn proximally from over the balloon, and withdrawn over the catheter shaft, exiting the patients body. The balloon catheter may then be withdrawn. In another method, the balloon catheter, with the device still mounted thereover, is withdrawn together with the device.

In yet another method, the radiation device is distally preloaded on a balloon catheter. The balloon catheter, having the irradiation device mounted thereon, is advanced to the site to be irradiated. The balloon is inflated in a manner similar to that described above. Distally preloading the device on a balloon allows for use of radiation devices with balloons where it would otherwise be difficult to advance the device distally over the balloon.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A device for providing radiation to vessel walls comprising:
   an elongate member having a proximal portion and a distal portion; and
   a plurality of radially expandable radiation emitting segments, each segment having a lumen for placement of a dilation balloon therein, said segments being operably connected to said elongate member distal portion, and said segments each having a longitudinal slit therethrough to allow radial expansion of said segments.

2. A device as recited in claim 1, wherein said segments have a less expanded state and a more expanded state, and said segments being biased to contract when expanded from said less expanded state to said more expanded state.

3. A device as recited in claim 2, wherein said radioactive material emits beta radiation.

4. A device as recited in claim 2, wherein said segments are substantially tubular and said segment slits allow for maneuvering an elongate shaft from the exterior to the interior of the lumen of said segments.

5. A device as recited in claim 4, wherein said slits include overlapping regions of said segments.

6. A device as recited in claim 4, wherein said segments are operably interconnected with at least one elongate member.

7. A device as recited in claim 1, wherein said radiation emitting segments includes Nickel-66.

8. A device for providing radiation to vessel walls comprising:
   an elongate member having a proximal portion and a distal portion; and
   a radially expandable elastic sleeve operably connected to said elongate member distal portion, said sleeve including radioactive material, and having a lumen therethrough for receiving a dilation balloon therein, said elastic sleeve expandable from an initial diameter to an expanded diameter, wherein said sleeve is biased to contract in diameter when said diameter is expanded.

9. A device as recited in claim 8, wherein said radioactive material emits beta radiation.

10. A device as recited in claim 8, wherein said sleeve includes a plurality of segments defined by slits.

11. A method for treating a stenosed vessel region comprising the steps of:
   providing a radiation device for emitting radiation to vessel walls, said device including an elongate member having a proximal portion and a distal portion, and a tubular member having a lumen therethrough, said tubular member being operably connected to said elongate member distal portion, said tubular member including radioactive material, said tubular member being radially expandable to a more expanded state and biased to return to a less expanded state;
   providing an inflatable balloon angioplasty catheter including an elongate shaft;
   advancing said balloon catheter to a site to be dilated;
   inflating said balloon, thereby dilating said vessel site;
   deflating said balloon at least partially;

positioning said radiation device tubular member over said catheter shaft so that said catheter shaft is within said tubular member lumen;

advancing said radiation device over said catheter shaft so that said balloon is positioned in said tubular member lumen;

inflating said balloon, thereby expanding said device tube and exposing said vessel walls to radiation;

deflating said balloon at least partially, thereby allowing said device tube to contract; and retracting said device.

12. A method as recited in claim 11 wherein said balloon catheter has a perfusion lumen extending through said balloon.

13. A method as recited in claim 12, wherein said tubular member includes a plurality of segments, said segments aligned longitudinally along said distal portion to form said tubular member lumen, wherein said segments are substantially tubular and have a longitudinal slit therethrough, said slit allowing for radially positioning said elongate shaft from the exterior to the interior of said lumen of said tubular member.

14. A method as recited in claim 12, wherein said tube comprises an elastomeric sleeve having radioactive material therein.

15. A method as recited in claim 12, wherein said radioactive material is a beta emitter.

16. A method for providing radiation to a vessel site comprising the steps of:

providing a radiation device including an elongate member having a distal portion and a plurality of radially expandable radiation emitting segments, each having a lumen therethrough operably connected to said distal portion, said segments being radially expandable to a more expanded state and biased to return to a less expanded state;

providing an inflatable balloon catheter including an elongate shaft;

advancing said balloon catheter to said site to be irradiated;

advancing said segments over said balloon, said balloon disposed within the lumen of said segments;

inflating said balloon, thereby expanding said segments and exposing said vessel walls to radiation;

deflating said balloon at least partially, thereby allowing said segments to contract; and retracting said balloon catheter.

17. A method as recited in claim 16, wherein said segments are disposed on said distal portion in spaced relation with said lumens aligned to receive said balloon therein.

18. A method as recited in claim 17, wherein said balloon catheter has a perfusion lumen through said balloon.

19. A method as recited in claim 18, wherein said segments are substantially tubular and have a longitudinal slit therethrough, said slit allowing for radially positioning an elongate shaft of said balloon catheter from the exterior to within the lumens of said segments.

20. A method as recited in claim 18, wherein said radioactive material is a beta emitter.

* * * * *